United States Patent [19]
Irth et al.

[11] Patent Number: 5,225,349
[45] Date of Patent: Jul. 6, 1993

[54] METHOD FOR ANALYTICAL SEPARATION OF INOSITOL PHOSPHATES WITH QUATERNARY AMINE AND METAL ION COMPLEX

[75] Inventors: Hubertus Irth, Amsterdam, Netherlands; Ruth Kornfeldt, Perstorp; Lars Persson, Hassleholm, both of Sweden

[73] Assignee: Perstorp AB, Perstorp, Sweden

[21] Appl. No.: 778,067

[22] PCT Filed: Jun. 15, 1990

[86] PCT No.: PCT/SE90/00423

§ 371 Date: Feb. 19, 1992

§ 102(e) Date: Feb. 19, 1992

[87] PCT Pub. No.: WO90/15989

PCT Pub. Date: Dec. 27, 1990

[30] Foreign Application Priority Data

Jun. 21, 1989 [DE] Fed. Rep. of Germany ....... 8902241

[51] Int. Cl.$^5$ .................. G01N 33/483; G01N 33/52
[52] U.S. Cl. .................................. 436/105; 436/103; 436/161; 422/70; 514/6
[58] Field of Search ................ 422/70; 435/155; 436/103, 105, 161; 514/6

[56] References Cited

PUBLICATIONS

Prestwich, S. A., Measurement of Picomole amounts of any inositol phosphate isomer separable by H.P.L.C. by means of a biol. assay., Biochemical J. (3)274, 1991, pp. 663–672.

Taylor, G. S. H.P.L.C. Analysis of Radiolabeled Inositol Phospaates, Anal. Biochemistry, 188, 1990 (1) pp. 118–120.

Wregett, K. A., A Rapid Sepa. Method for inositol phosphates and their Isomers, Biochem. J., 245 (3), 1987, pp. 655–660.

Dialog Inf. Service, file 351: World Patent Index, Acc. No. 3235145 & JP, A, 58109849 (Ashai Chemical IND KK) 30 Jun. 1983, Abstract.

Chemical Abstracts, vol. 107, No. 23, 7 Dec. 1987, D. B. McKay et al.: "Detection of polyols and sugars by cuprammonium ion in the presence of strong Base", pp. 302, Acc. No. 214459h, & Anal. Biochem, 1987, 165(2), 392–398.

*Primary Examiner*—James C. Housel
*Assistant Examiner*—Milton I. Cano
*Attorney, Agent, or Firm*—Stevens, Davis, Miller & Mosher

[57] ABSTRACT

Inositol phosphates and/or derivatives thereof are analytically separated, whereby a quaternary amine is mixed with an aqueous solution containing one or more inositol phosphates and/or derivatives thereof. The aqueous solution obtained is fed to an analytical column containing a solid non-polar phase and the different constituents thereof are detected.

15 Claims, 1 Drawing Sheet

METHOD FOR ANALYTICAL SEPARATION OF INOSITOL PHOSPHATES WITH QUATERNARY AMINE AND METAL ION COMPLEX

The present invention relates to a method for analytical separation of inositol phosphates and/or derivatives thereof and a means for analytical detection of inositol phosphates and/or derivatives thereof.

The research and development during the last few years relating to biologically active substances has to a certain extent been focused on inositol phosphates. These substances play an active role on the cellular level. At the same time there is a great potential to develop inositol phosphates and/or derivatives thereof to pharmaceutical substances. In order to optimally evaluate the reactions and the metabolism of inositol phosphates in cellular processes and to follow their resorption, mechanism of action and degradation when they are added to humans and animals it is necessary to have access to analytical methods of determination which make possible a careful and reproducible measurement of the inositol phosphates and/or derivatives thereof, in most cases, very low proportions of these compounds.

So far the development has resulted in chromatographic separation methods which however have serious limitations when low proportions of the compounds are to be separated. A non-specific absorption to glass, metal objects and certain materials of chromatography columns results in a non-existent possibility to analytically separate the substances.

The detection of inositol phosphates or derivatives thereof has also constituted a big problem since such compounds cannot be detected with conventional detectors such as UV detectors or electrochemical detectors.

One detection method is based on the determination of radio-actively labelled inositol phosphates. For natural reasons this determination method is limited to experiments which can be carried out in test tubes and of course it is not possible to use such tests on humans.

According to the present invention it has quite unexpectedly been possible to solve the above problem. The invention relates to a method for analytical separation of inositol phosphates and/or derivatives thereof. Then a quaternary amine is mixed with an aqueous solution containing one or more inositol phosphates and/or derivatives thereof.

Figure 1:
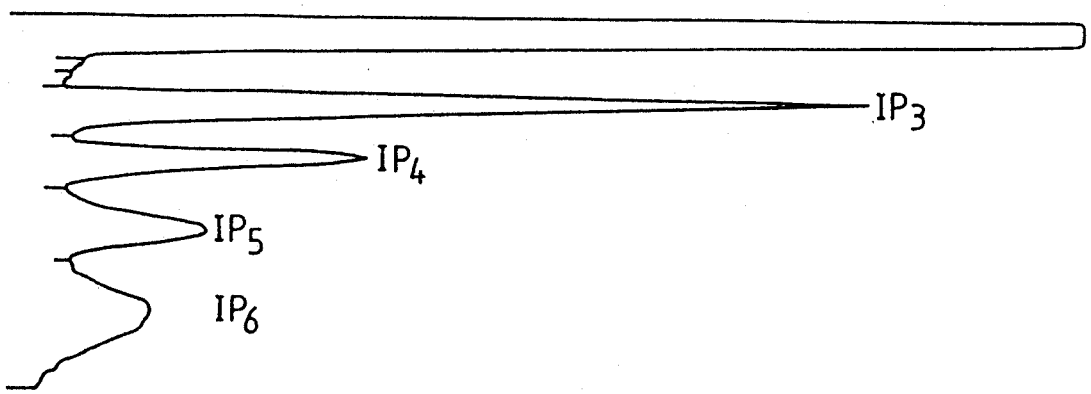
FIG. 1 illustrates the analytical separation of inositol trisphosphate, inositol tetraphosphate, inositol pentaphosphate and inositol hexaphosphate obtained in Example 1.

The solution obtained is fed into an analytical column containing a solid phase of a non-polar kind, whereby a separation of the different constituents of the fed solution is obtained since the constituents pass through the column at different velocities and are then detected in a suitable way.

The invention makes a separation of the constituents possible also when these are present at very low proportions since the method disclosed eliminates the previously known problems with a non-specific absorption.

From the admixture of a quaternary amine as mentioned above, positively charged ions are obtained which form non-polar ion pairs together with inositol phosphates and/or derivatives thereof.

The aqueous solution can consist of water containing samples of biological origin. Here blood-plasma, blood-serum, blood, urine, faeces, tissue extracts or the like can be mentioned. Sometimes the water containing samples should be pretreated or purified to minimize the interference of proteins, lipids and organic and inorganic substances.

This pretreatment can include a precipitation step for example by the addition of perchloric acid to decrease disturbances from proteins according to known techniques. In certain cases the ionic strength of the aqueous solution can restrict the analytical separation from working optimally. Here different techniques for decreasing the ionic strength of the sample can be used. For instance, if the ionic strength is caused by perchlorate ions the amount of these ions can be decreased by the addition of potassium hydroxide.

According to another method the aqueous solution can be fed through a column for example of ion exchange type. If the elution is carried out in a suitable way for example with an eluent which is highly volatile a subsequent evaporation can eliminate a too high ionic strength.

Sometimes a preconcentration of the aqueous solution containing the inositol phosphates and/or derivatives thereof can be carried out to get a smaller volume containing a certain amount of the substance to pass the column. This process decreases band broadening which will otherwise arise. Such a band broadening will decrease the sensitivity of the analytical separation system.

The preconcentration technique can consist of bringing an ion pair formed between the quaternary amine and the inositol phosphates to fasten to a small column for example 10 mm×2 mm silicon based column of a non-polar type, before an eluation to the analytical column takes place for separation of the constituents present.

The content of inositol phosphates and/or derivatives thereof in the original aqueous solution that can be analytically separated according to the present invention is between 0.01 ppb and 100 ppm, preferably between 0.1 ppb and 50 ppm and most preferably between 0.5 ppb and 20 ppm.

When a preconcentration step is used the content of inositol phosphates and/or derivatives thereof in the solution fed into the analytical column is between 0.05 ppb and 500 ppm, preferably between 0.5 ppb and 250 ppm and most preferably between 2.5 ppb and 100 ppm.

According to the present invention an improvement of the analytical separation can be obtained by using an eluent with a pH between 5 and 9, preferably between 6 and 8, for elution of the aqueous solution through the column.

For example the quaternary amine used according to the invention can consist of tetrabutyl ammonium ion, tetrapentyl ammonium ion or tetrahexyl ammonium ion. Moreover, possibly other positively charged ions such as benzalconium ion or the like can be used. Suitably, the proportion of the quaternary amine is 0.1 mM to 20 mM, preferably 0.5 mM to 10 mM.

According to one embodiment of the invention another solution containing one or more low molecular anions is added to the aqueous solution used before the passage through the analytical column. The anions have a molecular weight less than 200 g/mol and can consist of sulphate, phosphate, pyrophosphate or the like. This addition improves the analytical separation ability of the solid phase whereby a more efficient separation of the constituents is brought about.

According to the present invention the constituents are detected in a suitable way after the passage through the column. Suitably the detection can be brought about by refractive index measurement, by detection of the constituents by means of light scattering technique, by carrying out measurements in the ultra-violet area after an addition of complex forming metal ions such as copper ions or by fluorescence technique. The fluorescence technique meant here relates to the following principle.

After the analytical separation of the constituents by passage through the analytical column, a reagent solution (so-called post-column reaction), consisting of a metal ion complex, comprising in addition to a metal ion also a substance which has fluorescent properties when present unbonded to metal ions, is continuously added to the solution leaving the column. When the substance is bonded to metal ions the complex has no fluorescent properties.

The metal ion complex is selected in such a way that the metal ions at contact with the inositol phosphates and/or derivatives thereof are transferred to form a metal ion inositol phosphate complex, whereby the fluorescent substance is released. The stoichiometry and the equilibrium of the reaction is selected in such a manner that a specific amount of inositol phosphate or a derivative thereof results in a corresponding amount of the substance with fluorescent properties.

In a preferred method for analytical separation of inositol phosphates and/or derivatives thereof according to the invention, the detection is made by the fluorescent technique.

The invention also relates to a means for analytical detection of inositol phosphates and/or derivatives thereof. The means consists of a metal ion complex which per se has no fluorescent properties but at the contact with a solution of inositol phosphates or derivatives thereof causes a bonding between the metal ions and the inositol phosphates and/or derivatives thereof. The substance which originally formed a complex with the metal ions is then released in free form, i.e. not as a metal ion complex with fluorescent properties.

Preferably, the detection is carried out in such a way that the means according to the invention is continuously added to the liquid stream which has passed the analytical column which makes a separation of the constituents possible.

This so-called post-column reaction must meet certain fundamental requirements in order to work to detect inositol phosphates and/or derivatives thereof. The means must have such a reactivity that a complete reaction is attained within a very short period. All components of the means must be compatible with the components which are to be separated during passage through the column. The metal ion complex which is present in the means must consist of components which are rather strongly bonded to each other to avoid the formation of a background fluorescence which decreases the sensitivity of the method. A general desire is that the amount of the complex constant of the complex should be at least $10^8$.

The means should be selected in such a way that a considerably stronger metal ion inositol phosphate complex and/or a complex to a derivative of the inositol phosphate is formed as compared to the original metal ion complex in order to get a rapid and complete yield of the component which is bonded to the metal ions.

The metal ions which bind strongly to inositol phosphate and/or derivatives thereof can be found in the group of metal ions which have a charge of three or more. Also some divalent metal ions bind so strongly to inositol phosphates and/or derivatives thereof that they are applicable according to the invention. Accordingly, Fe (III), Cr (III), Al (III), Pb (II) and Ni (II) constitute examples of metal ions which have properties that meet the above requirements.

The selection of so-called functional groups included in the so-called ligands that preferably constitute the second part of the metal ion complex is mainly directed to carboxy and hydroxy groups. However, other metal ion bonding functional groups can also be present.

The pH is a critical parameter in a solution where the components present should be detected by fluorescence. To get optimal reaction conditions and a maximum measuring signal the pH should be between 4 and 9, preferably 5 and 8.

Thus, with respect to bondings to Fe (III), for instance mono-hydroxy compounds are usually not relevant since their pKa values are often higher than 8.

On the other hand many dihydroxy compounds and acetate containing compounds such as imino diacetate compounds are not useful since they form a complex which binds Fe (III) stronger than inositol phosphates and/or derivates thereof.

According to the invention it has quite unexpectedly turned out that N-alkylimino acetate containing compounds meet the properties disclosed above. N-alkylimino compounds containing carboxy functions other than acetate are also useful according to the invention. Also sulfosalicylic acid or chromotropic acid or derivatives thereof are applicable according to the invention.

Among the N-alkylimino acetate containing substances, N-methylimino acetate containing compounds such as methylcalcein and methylcalcein blue are preferred.

According to a preferred embodiment of the invention the means for analytical detection of inositol phosphates and/or derivatives thereof consists of Fe (III) and methylcalcein blue (MCB).

A temperature above 40° C. and a pH above 5 are preferred to get optimum reaction conditions. Often the metal ion complex is added as a solution containing water and organic solvents such as tetrahydro-furan, methanol, ethanol or acetonitrile.

The concentration of the metal ion complex and the proportion between the metal ion and the second component of the complex can vary. When the metal ion complex consists of Fe (III)/MCB the concentration of MCB can be between 0 5 µM and 10 mM, preferably between 1 µM and 1 mM and most preferably between 2 µM and 0.5 mM. The content of Fe (III) can vary from one tenth of the content of MCB to ten times the content of MCB calculated on molar basis.

The means according to the invention is used for analytical detection of inositol phosphates or derivatives thereof where the content of these substances amounts to 0.01 ppb to 100 ppm, preferably 0.1 ppb to 50 ppm and most preferably 0.5 ppb to 20 ppm.

The invention is illustrated further in the embodiment examples below but these examples do not constitute a limitation of the invention.

Example 1 relates to an analytical separation of inositol phosphates by means of an ion pair system while example 2 illustrates a detection of analytical amounts of inositol phosphates.

EXAMPLE 1

One ml of an aqueous solution containing 5 μg of a mixture of inositol phosphates was injected into a chromatographic system where the analytic column used was a Nucleosil $RP_{18}$ column (200×4 mm) and the eluent which passed the column consisted of methanol/tetrahydrofuran/5 mM trishydroxymethyl aminomethan solution adjusted to pH 7.0 with hydrochloric acid (Tris buffer) and 3 mM tetrapentyl bromide solution: 50/5/45 per cent by volume.

A post-column reaction was carried out to bring about a detection system based on fluorescense technique. A solution of methanol/Tris buffer: 95/5 per cent by volume and 10 μM methyl calcein blue and 5 μM iron (III) nitrate was added continuously to the eluent coming out of the column.

After the reaction the solution was allowed to pass a fluorescence detector for detection of the inositol phosphates which had been separated in the analytical column.

The analytical separation of inositol trisphosphate ($IP_3$), inositol tetraphosphate ($IP_4$), inositol pentaphosphate ($IP_5$) and inositol hexaphosphate ($IP_6$) obtained is illustrated in FIG. 1.

EXAMPLE 2

Two aqueous solutions contained 180 ng/ml and 36 ng/ml respectively of inositol trisphosphate ($IP_3$). First 0.5 ml of the solution containing 180 ng/ml was injected into an analytical system where the analytical column used was a Hypersil ODS column (200×4.6 mm) and where the eluent consisted of methanol/tetrahydrofuran/5mM trishydroxymethyl aminomethan solution adjusted to pH 6.8 with hydrochloric acid (Tris buffer) and 20 mM tetrabutyl ammonium bromide 30/3/67 per cent by volume.

After the chromatographic column a solution was added which made detection by means of fluorescence technique possible. This solution consisted of methanol/Tris buffer: 95/5 per cent by volume and 10 μm methylcalcein blue and 5 μm iron (III) nitrate.

The post-column reaction was carried out at 60° C. The excitation wavelength used in the fluorescence detector was 318 nm and the emission wavelength was 440 nm.

The above procedure was repeated with 0.5 ml of the aqueous solution containing 36 ng/ml.

Figure 2A:
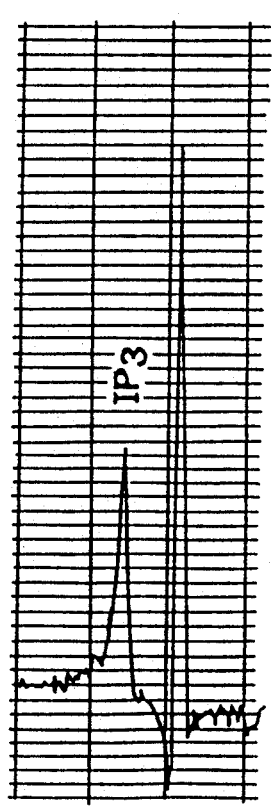
FIG. 2a shows the proportion of inositol trisphosphate detected in Example 2 when the starting solution contained 36 ng/ml of inositol trisphosphate.
Figure 2B:
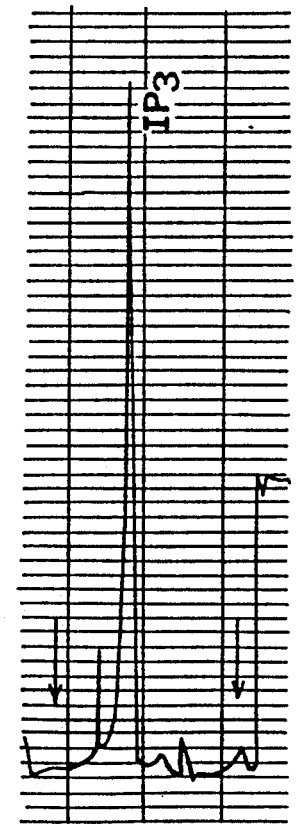
FIG. 2b shows the proportion of inositol trisphosphate detected in Example 2 when the starting solution contained 180 ng/ml of inositol trisphosphate.

The detection of these small proportions of $IP_3$ is illustrated in Chromatograms in FIGS. 2a and 2b.

We claim:

1. A method for analytical separation of inositol phosphates, derivatives of inositol phosphates or a combination of inositol phosphates and derivatives of inositol phosphates, comprising mixing a quaternary amine with an aqueous solution containing one or more members selected from the group consisting of inositol phosphates, derivatives of inositol phosphates and combinations of inositol phosphates and derivatives of inositol phosphates, feeding the solution obtained into an analytical column containing a solid non-polar phase, whereby the fed solution is separated into its different constituents since the constituents pass through the column at a different velocity, and detecting the separated inositol phosphates and derivatives of inositol phosphates of the aqueous solution.

2. A method according to claim 1, wherein the aqueous solution containing one or more members selected from the group consisting of inositol phosphates, derivatives of inositol phosphates and combinations of inositol phosphates and derivatives of inositol phosphates is purified to remove any impurities before the mixing with quaternary amine.

3. A method according to claim 1, wherein the content of the one or more members of the group consisting of inositol phosphate, derivatives of inositol phosphate and combinations of inositol phosphate and derivatives of inositol phosphate in the original aqueous solution is in the range of 0.1 ppb–50 ppm.

4. A method according to claim 3, wherein the content is in the range of 0.5 ppb–20 ppm.

5. A method according to claim 1, wherein the content of the one or more members of the group consisting of inositol phosphate, derivatives of inositol phosphate and combinations of inositol phosphate and derivatives of inositol phosphate in the aqueous solution fed to the analytic column is in the range of 0.5 ppb–250 ppm.

6. A method according to claim 4, wherein the content is in the range of 2.5 ppb–100 ppm.

7. A method according to claim 1, wherein the aqueous solution used has a pH in the range of 5–9.

8. A method according to claim 5, wherein the pH of the aqueous solution is in the range of 6–8.

9. A method according to claim 1, wherein the quaternary amine is tetrabutyl ammonium ion, tetraphenyl ammonium ion or tetrahexyl ammonium ion.

10. A method according to claim 1, wherein the separation in the column of the different constituents is improved by treatment of the solid non-polar phase with an aqueous solution containing one or more different anions with a molecular weight less than 200.

11. A method according to claim 1, wherein the aqueous solution contains at least one member selected from the group consisting of blood-plasma, serum, blood, urine, faeces and tissue extracts.

12. A method according to claim 1, wherein a reagent which makes detection by fluorescence techniques possible is added to the solution when the solution passes out of the column.

13. A composition for analytical detection of inositol phosphates, derivatives of inositol phosphates and combinations of inositol phosphates and derivatives of inositol phosphates, comprising a complex of metal ions and a compound selected from the group consisting of sulfosalicylic acid, chromotropic acid or N-methylimino acetate containing substance and derivatives thereof which per se has no fluorescent properties but which causes, when in contact with inositol phosphates, derivatives of inositol phosphates and combinations of inositol phosphates and derivatives of inositol phosphates, the metal ions to bond whereupon a fluorescent substance is released.

14. A composition according to claim 10, wherein the metal ions of the complex are selected from the group consisting of iron, chromium and aluminum.

15. A composition according to claim 10 comprising a complex of Fe (III) and methyl calcein blue.

* * * * *